United States Patent [19]

Zakroczymski

[11] Patent Number: 5,030,211

[45] Date of Patent: Jul. 9, 1991

[54] MEANS FOR OPENING A FLUID INLET VALVE OF A DISPOSABLE CONTAINER

[75] Inventor: Adam K. Zakroczymski, Antioch, Ill.

[73] Assignee: Plasco, Inc., Gurnee, Ill.

[21] Appl. No.: 421,789

[22] Filed: Oct. 16, 1989

[51] Int. Cl.[5] .......... A61M 3/00; B65D 33/00

[52] U.S. Cl. .......... 604/262; 604/403; 383/35

[58] Field of Search .......... 604/403, 408, 257, 262; 383/43, 44, 42, 35, 49

[56] References Cited

U.S. PATENT DOCUMENTS

| | | | |
|---|---|---|---|
| 3,473,532 | 10/1969 | Eisenberg | 383/35 |
| 3,724,461 | 4/1973 | Eisenberg | 383/35 |
| 3,734,154 | 5/1973 | Polk | 383/35 |
| 4,646,586 | 7/1989 | Bruno | 383/335 |
| 4,758,099 | 7/1988 | Branson | 383/35 |
| 4,838,874 | 6/1989 | Eisenberg | 604/262 |

*Primary Examiner*—Stephen C. Pellegrino
*Attorney, Agent, or Firm*—Jerome Goldberg

[57] ABSTRACT

A container for fluids having a valve positioned inside and adjacent to a fluid supply opening. The valve has an open condition to provide a fluid inlet passageway and a closed condition to close the fluid inlet passageway. An outer pocket is secured on the outside of the container, isolated from the fluid supply opening. Upon opening the pocket outward, the valve moves responsively from the closed condition to the open condition.

8 Claims, 1 Drawing Sheet

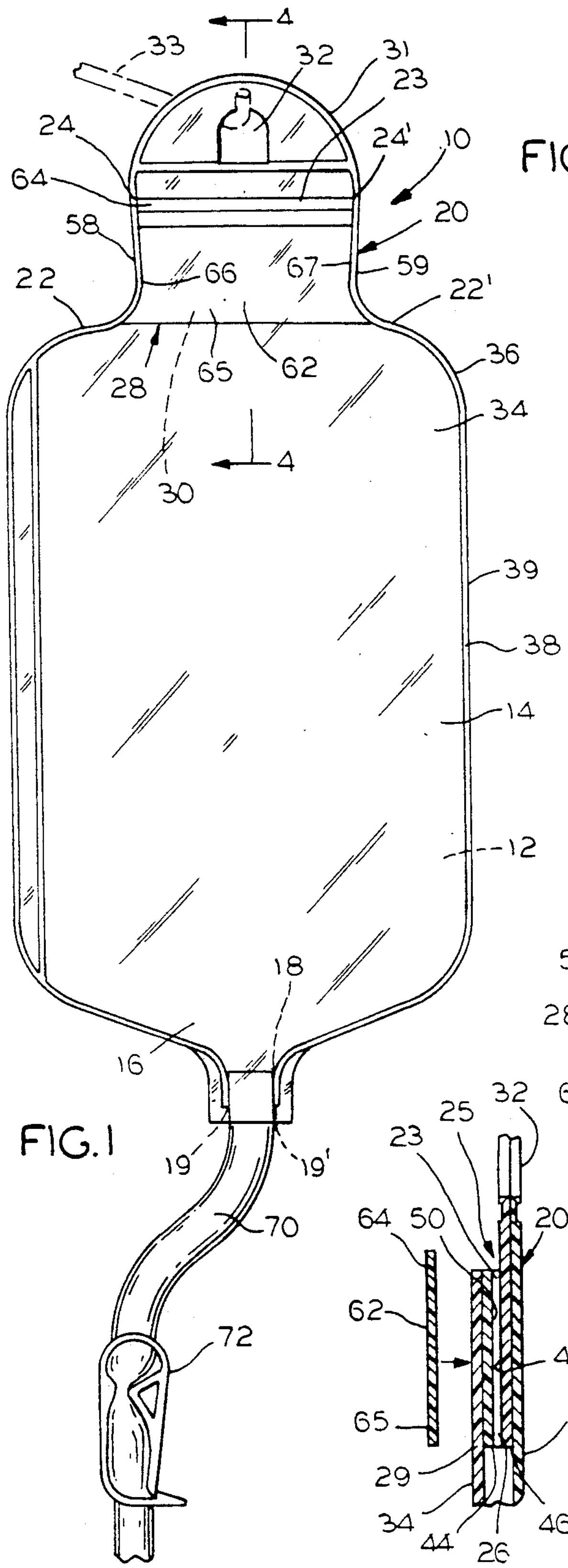
FIG.1
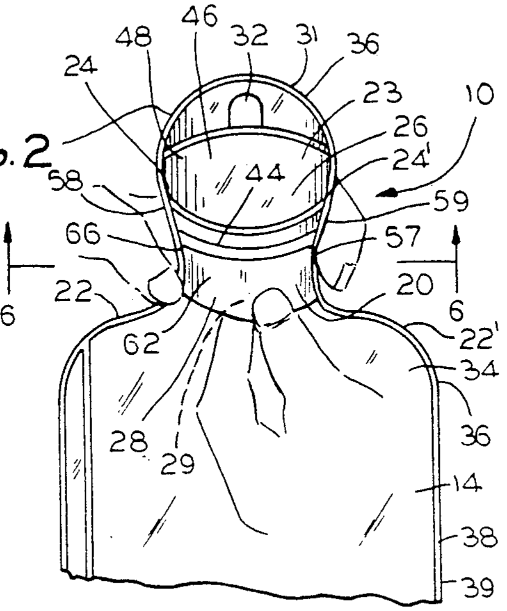
FIG. 2
FIG.4
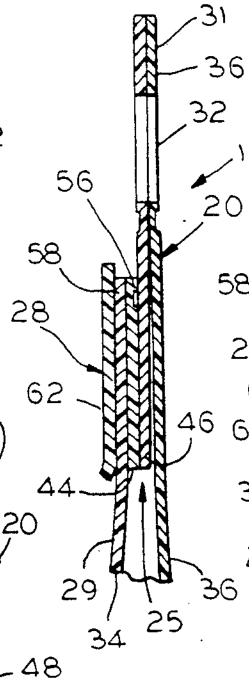
FIG.5
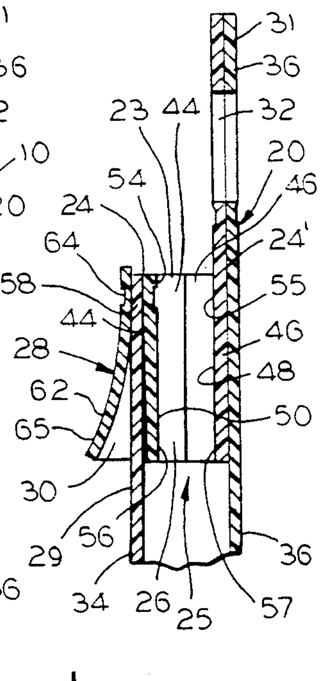
FIG.3
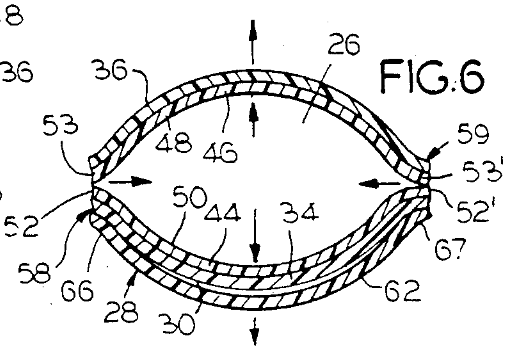
FIG.6

MEANS FOR OPENING A FLUID INLET VALVE OF A DISPOSABLE CONTAINER

BACKGROUND OF THE INVENTION

This invention relates g a disposable fluid bag or container having a fluid inlet valve, and more specifically relates to means for opening a fluid inlet valve of a disposable container.

Disposable fluid bags are extensively used as an enema or douche bag. They are also used widely in hospitals and nursing homes, to store and hold medicines, nourishment, vitamins etc. The fluids may be transferred to the patient through a conventional gravity flow system. It is imperative to maintain these bags free of contamination during use, particularly when the user is very ill and may have a seriously impaired immune system.

A flexible container previously used such as disclosed in U.S. Pat. No. 4,838,874, June 13, 1989, entitled, "Fluid Container Having A One Way Valve", by the inventor Melvin I. Eisenberg, included a front flexible wall and a rear flexible wall sealed together along marginal portions thereof to define a body for holding fluid and unsecured along other portions thereof to provide an inlet fluid supply opening. The upper part of the container was formed into a neck configuration which included the fluid supply opening at the outer end thereof.

A valve was positioned inside the neck of the container adjacent the fluid supply opening between the front and rear walls, to provide a fluid inlet passageway when the valve was open and to close the fluid inlet passageway when the valve was closed. The valve comprised an inner sheet and a spring sheet opposed to each other. The inner sheet was normally in contact with the spring sheet to close the valve. Upon the application of an inward force at opposite points on the outside of the neck of the container, the inner sheet and the spring sheet bowed outward and away from each other to open the valve, so that fluid could pass between the inner sheet and spring sheet and into the body of the container.

The spring sheet was formed from a rigid type flexible plastic material, whereas the inner sheet was formed from a flexible soft and pliable plastic material which tended to cling, and frequently tightly engaged the spring sheet when the valve was closed. When this occurred, the container did not readily open.

Moreover, the nurse, nurse's aid or other attending medical person, when encountering difficulty in opening the valve upon pressing inward at opposed points on the neck of the container, would often times reach inside the neck of the container and pull the clinging inner sheet away from the spring sheet with his or her finger(s). This increased the likelihood of contaminating the container, which, if the container became contaminated, could be extremely detrimental to the health and well being of the patient.

The subject invention overcomes the afore-mentioned problems and affords positive means, isolated from the fluid supply opening, for easily and quickly opening the inlet fluid valve of the disposable container.

SUMMARY OF THE INVENTION

The fluid container of this invention flexible wall confronting a rear flexible wall, sealed along marginal portions and unsecured along other portions thereof for providing a fluid supply inlet opening. The upper part of the container including the fluid inlet supply opening is formed into a neck configuration. A valve comprising a flexible inner sheet and a spring sheet which is more rigid than the inner sheet, is positioned inside the neck of the container adjacent the inlet opening. The valve is normally closed when the inner sheet is in contact with the spring sheet, and is open when the inner sheet and spring sheet are spread apart to provide a fluid inlet passageway.

A strip of flexible material extends laterally across the outside of the front wall at the neck of the container. The strip is attached to the front wall at the upper edge and also at the opposed side edges and unattached at the bottom edge thereof, to form an outer pocket. The inside of the pocket is isolated from the fluid supply opening. Thus, by holding the neck of the container with one hand, and opening the pocket and applying an outward force with the other hand, the inner sheet of the valve in response is disassociated from the spring sheet of the valve for opening the fluid inlet passageway.

It is therefore a primary object of the invention to provide a disposable container having a one way fluid inlet valve, and including means for preventing contamination of the container when opening the valve prior to inserting fluid into the container.

Another object is to provide simplified and quick means for opening the valve of the container prior to filling the container with fluid.

Another object is to provide means for opening a fluid container, isolated from the fluid inlet supply opening of the container.

It is a primary feature of the invention to provide an outer pocket positioned on the outside of a container, adjacent to but isolated from a fluid inlet valve, so that the fluid inlet valve opens in response to opening the pocket.

Another feature is to provide a strip of material positioned on the outside of the container and attached at the opposed sides thereof to the marginal side edges of an inner sheet and spring sheet of a fluid inlet valve and attached at the top of the strip to the top edge of the inner sheet, so that upon pulling the strip outward the inner sheet and spring sheet in response disassociate from each other to open the valve.

BRIEF DESCRIPTION OF THE DRAWINGS

Referring to the drawings in which the same characters of reference are employed to indicate corresponding similar parts throughout the several figures of the drawings:

FIG. 1 is a front elevational view of the fluid container, embodying the principles of the invention;

FIG. 2 is a fragmentary perspective view of the fluid container showing the fluid inlet opening being opened by opening the pocket on the outside of the container;

FIG. 3 is a fragmentary sectional view showing a strip of material spaced from the outside of the fluid container prior to being attached thereto to form the outer pocket;

FIG. 4 is a fragmentary sectional view taken on the plane of the line 4—4 in FIG. 1, and showing the pocket, the one way valve and the fluid inlet passageway in a closed condition;

FIG. 5 is a fragmentary sectional view similar to FIG. 4, but showing the pocket, valve and fluid inlet passageway in an open condition; and FIG. 6 is a sectional top view, taken on the plane of the line 6—6 in FIG. 2, and showing the valve and the fluid inlet passageway in an open condition.

DESCRIPTION OF PREFERRED EMBODIMENT

Referring now more particularly to FIGS. 1 and 2 of the drawing, the reference numeral 10 indicates generally a fluid disposable bag or container which may be used for storing and containing fluids 12 including medicines, vitamins and food nourishment. The container 10 may also function as an enema or douche bag. The fluids in the bag may be transferred by a conventional gravity flow system to the patient in the hospital or in a nursing home.

The fluid bag 10 comprises a body portion 14 for storing or containing the fluid 12 and including a bottom part 16 having a fluid outlet opening 18 between points 19,19', a neck portion 20 extending upward from shoulders 22, 22' and having a fluid inlet supply opening 23 between points 24,24'.

A one way valve indicated generally by the reference numeral 25 is positioned inside the neck portion 20 adjacent the fluid inlet opening 23. The valve 25 provides a fluid inlet passageway 26 (FIGS. 2 and 5) when the valve is open and closes the fluid inlet passageway 26 when the valve is closed (FIG. 4).

A pocket indicated generally by the reference numeral 28 is secured on the front side 29 of the neck portion 20 of the bag 10. The valve 25 is opened by applying an outer force (FIG. 2) on the inside 30 (FIG. 5) of the pocket 28, to move the pocket from a closed position (FIG. 4) to an open position (FIGS. 5 and 6).

A handle 31 extends upward from the neck portion 20 for holding or carrying the bag 10. An oblong hole 32 is formed in the handle 31, sized to receive a finger for holding when carrying or lifting the bag, and also to be used for hanging the bag 10 on a rod 33 in a vertical position (FIG. 1).

The bag 10 comprises a flexible front wall 34 (FIGS. 1 and 2) opposed and confronting a flexible rear wall 36 (FIGS. 4 and 5). Preferably, the walls 34,36 are formed from a heat sealable, flexible synthetic plastic material, such as a polyvinyl chloride material.

The walls are heat sealed together along corresponding marginal portions 38,39 respectively of the front wall 34 and rear wall 36 to define the body portion 14 and the neck portion 20; unsecured along corresponding lower marginal portions to define the fluid outlet opening 18 between points 19,19'; and also unsecured along corresponding upper marginal portions to define the fluid inlet opening 23 between the points 24,24'.

The valve 25 includes a flexible inner sheet 44 and a spring sheet 46 interposed between the front wall 34 and the rear wall 36 inside the neck portion 20 (FIGS. 4 and 5). The front face 48 of the spring sheet 46 is opposed to the rear face 50 of the inner sheet 44 (FIG. 6). The inner sheet 44 may be formed from a material similar to the material used for the walls 34,36 such as a flexible and pliable polyvinyl chloride material. The spring sheet 46 may be a sheet of rigid and resilient& polyvinyl chloride material.

The marginal side edges 52,52' of the inner sheet 44 are attached respectively to the marginal side edges 53,53' of the spring sheet 46. The inner sheet 44 and the spring sheet 46 are unattached to each other at the corresponding top parts 54 and 55 and also unattached at their corresponding bottom parts 56,57, to form a sleeve like configuration.

The marginal side edges 52,53 of the inner sheet 44 and spring sheet 46 are also attached to one side 58 (includes marginal portions 38,39 of the front and rear walls 34,36) of the neck 20, and the marginal side edges 52',53' of the inner sheet 44 and spring sheet 46 are also attached to the opposite side 59 (also includes marginal portions 38,39 of the front and rear walls 34,36) of the neck 20.

When the inner sheet 44 and the spring sheet 46 of the valve 25 are in contact with each other, the valve 25 is closed to close the inlet passageway 26. When the inner sheet 44 and the spring sheet 46 are spread apart, the valve is open to provide the fluid inlet passageway 26 into the body portion 14 of the bag 10.

The pocket 28 includes a substantially rectangular strip of material 62 having a top 64, bottom 65 and opposed sides 66,67. The top 64 and sides 66,67 are attached to the neck 20 of the container 10, and the bottom 65 is unattached to afford access inside 30 of the pocket 28.

The side 66 of the strip 62 is attached to the marginal side edges 52,53 respectively of the inner sheet 44 and spring sheet 46 and to the side 58 of the neck 20 of the container, and the opposite side 67 is attached to the marginal side edges 52',53' respectively of the inner sheet 44 and the spring sheet 46 and to the opposite side 59 of the neck 20 of the container.

The top part 54 of the inner sheet 44 is attached to the front wall 34 and also to the top 64 of the strip 62. The top part 55 of the spring sheet 46 is attached to the rear wall 36.

A feed tube 70 extends inside the outlet opening 18 and is in communication with the interior of the container 10. An on-off clamp member 72 controls the flow of fluid 12 out from the container 10 and through the feed tube 70.

The container 10 is normally closed and the pocket 28 is also normally closed. To open the container 10, the opposite sides 58,59 of the neck 20 of the container are held with one hand, and the bottom 65 of the pocket 28 is lifted away from the front side 29 of the front wall 34 with the other hand to access the inside 30 of the pocket. The strip 62 is then pulled outward, causing the opposite sides 58,59 of the neck 20 (and also the opposite marginal side edges 52,52' of the inner sheet 44 and the marginal opposite side edges 53,53' of the spring sheet 46 and the opposite sides 66,67 of the strip 62 which are attached respectively to the opposed sides 58,59 of the neck) to move inwardly and the inner sheet 44 and the spring sheet 46 between the opposite sides 58,59 of the neck 20 to bow outwardly away from each other and thereby opening the fluid inlet passageway 26 to the inside of the body portion 14.

When the outward force is removed from the strip 62 of the pocket 28, the spring sheet 46 moves inwardly, causing the opposite sides 58,59 of the neck 20 to move outwardly to pull the inner sheet 44 in contact with the spring sheet 46, thereby closing the fluid inlet passageway 26.

Thus, when forcing the strip 62 of the pocket 28 outwardly, the valve 25 switches from the closed condition to the open condition, to permit fluid to be inserted into the container. When the force is removed from the strip 62, the valve 25 closes to shut off the fluid inlet passageway 26. By utilizing the pocket 28 opening arrangement as aforedescribed, which is isolated from the fluid inlet opening 23, the valve 25 is easily and quickly switched to the open condition for inserting fluid 12 into the container 10. After the valve 25 is closed, the fluid may flow between the front wall 34 and the inner sheet 44 and between the rear wall 36 and the spring sheet 46 to more securely close the valve 25.

Various modifications of the invention described herein are within the spirit and scope of the invention, the scope of which is limited solely and defined by the appended claims.

I claim:

1. A container for fluid comprising:

a front flexible wall and a rear flexible wall sealed together along marginal edges thereof to provide a pouch for fluids and unsecured along other marginal portions thereof to provide a fluid supply opening;

a valve positioned inside said pouch and adjacent to said fluid supply opening, said valve having an open condition for opening a fluid inlet passageway from the supply opening to the inside of the pouch and a closed condition for closing said fluid inlet passageway;

said valve including a flexible inner sheet and a spring sheet, said inner sheet contacting said spring sheet for closing said inlet passageway, said inner sheet being spaced from said spring sheet to open said inlet passageway and permitting fluid to flow between the inner sheet and the spring sheet, said inner sheet and spring sheet being attached to each other along opposite side margins thereof and unattached to each other at the top and bottom ends thereof to form a sleeve like configuration; and a strip of material positioned on the outside of one of said walls and having a top end, a bottom end and opposed sides, the sides of the strip being attached respectively to the opposite side margins of the inner sheet and spring sheet and to spaced apart locations on said one wall, the moving of said strip between the sides thereof away from said one wall causing said inner sheet between the opposite side margins thereof to move outwardly in one direction and said spring sheet between the opposite side margins thereof to move in the opposite direction and thereby opening the valve.

2. A container of claim 1, wherein the upper part of said container is formed to a neck configuration having a front face and a rear face sealed together along marginal edges on one side of the neck and also sealed together along the marginal edges at the opposite side of the neck, said strip having a top, a bottom and opposed sides and extending laterally across one of said faces, one side of said strip being attached to the marginal edges on one side of the neck and the other side of the strip being attached to the marginal edges on the opposite side of the neck.

3. A container for fluid comprising:

a front flexible wall and a rear flexible wall sealed together along marginal edges thereof and unsecured along other marginal portions thereof to provide a pouch for fluids;

a fluid supply opening formed at said unsecured marginal portions of the walls at the top area of the pouch;

a valve positioned inside said pouch and adjacent to said fluid supply opening, said valve having an open condition for opening a fluid inlet passageway from the supply opening to the inside of the pouch and a closed condition for closing said fluid inlet passageway;

said valve including a flexible inner sheet and a spring sheet, said inner sheet contacting said spring sheet for closing said inlet passageway, said inner sheet being spaced from said spring sheet to open said inlet passageway for permitting fluid to flow between the inner sheet and the spring sheet, said inner sheet and said spring sheet being attached to each other along opposite side margins thereof and unattached to each other at the top and bottom ends thereof to form a sleeve like configuration;

a strip of material secured to the outside of said pouch and opposed to said inner sheet, one of said pouch walls being sandwiched between said strip and the inner sheet, said strip having a top, a bottom and opposed sides, the sides of the strip being attached respectively to the opposite side margins of the inner sheet and spring sheet and the top of said strip being attached to the top of said inner sheet, so that the moving of said strip outwardly causing said inner sheet to bow outwardly in one direction and said spring sheet to bow outwardly in the opposite direction between the opposite marginal edges of the inner sheet and the spring sheet for opening said valve.

4. The container of claim 3, wherein the upper part of said one wall is attached to the top end of the inner sheet, and the top of said strip is attached to said upper part of said one wall.

5. The container of claim 3, wherein said strip of material is flexible and normally opposed to and in contact with the outer surface of said one wall.

6. A container for fluids comprising:

a front flexible wall and a rear flexible wall sealed together along marginal edges thereof to define a pouch for holding fluid and unsecured along portions thereof to provide a fluid supply opening;

a valve positioned in said container and adjacent to said fluid supply opening to provide a fluid inlet passageway to the inside of the container when the valve is open and to close the inlet passageway when the valve is closed;

said valve including a flexible inner sheet and a spring sheet, said inner sheet being spaced from said spring sheet to open said inlet passageway and permitting fluid to flow between the inner sheet and the spring sheet, said inner sheet contacting said spring sheet to close said inlet passageway, said inner sheet and spring sheet being attached to each other along opposite side margins thereof in a sleeve like configuration and unattached to each other at the top and bottom ends thereof, said inner sheet being attached to one of said walls between said side margins and said spring sheet being attached to said other wall between said side margins; and a strip of material positioned on the outside of said one wall, said strip including a top, a bottom and opposed sides, the top of the strip between the sides thereof being attached to the top end of the inner sheet and to said one wall, said sides of the strip being attached respectively to the opposite marginal edges of the front and rear wall and said sides of the strip also being attached respectively to the opposite side margins of the inner sheet and the spring sheet, the pulling of said bottom of the strip outward between the sides thereof causing said inner sheet to spread apart from said spring sheet for opening said valve.

7. The container of claim 6, wherein:

the opposite side margins of said inner sheet and spring sheet are attached respectively to opposed marginal edges of the front and rear walls and to said opposed sides of the strip.

8. A container for fluids comprising:

a front wall and rear wall sealed together along marginal edges thereof to provide a pouch for holding fluid and unsecured along portions thereof to provide a fluid supply opening;

a valve positioned in said container and adjacent to said fluid supply opening to provide a fluid inlet passageway to the inside of the pouch when the valve is open and also to close the inlet passageway when the valve is closed;

said valve including a flexible inner sheet and a spring sheet, said inner sheet being spaced from the spring sheet to open said inlet passageway and permitting fluid to flow between the inner sheet and spring sheet, said inner sheet contacting said spring sheet to close the inlet passageway, said inner sheet and spring sheet being attached to each other along opposite side margins thereof in a sleeve like configuration and unattached to each other at the top and bottom thereof, said inner sheet being attached to the front wall between said side margins and said spring sheet being attached to said rear wall between said side margins; and a strip of material positioned on the outside of one of said walls, said strip including a top end, a bottom end and opposed sides, said sides of the strip being attached respectively to the opposite side margins of the spring sheet and the inner sheet, the pulling of said strip outwardly between said sides of the strip causing said inner sheet and spring sheet to spread apart from each other for opening said valve.

* * * * *